United States Patent [19]

Meier et al.

[11] Patent Number: 5,003,079
[45] Date of Patent: Mar. 26, 1991

[54] PROCESS FOR THE PREPARATION OF BENZIMIDAZOLONES

[75] Inventors: Michael Meier, Frankfurt am Main; Günther Semler, Kelkheim, both of Fed. Rep. of Germany

[73] Assignee: Hoechst Aktiengesellschaft, Frankfurt am Main, Fed. Rep. of Germany

[21] Appl. No.: 441,160

[22] Filed: Nov. 24, 1989

[30] Foreign Application Priority Data

Nov. 25, 1988 [DE] Fed. Rep. of Germany ....... 3839743

[51] Int. Cl.$^5$ .......................................... C07D 209/34
[52] U.S. Cl. .................................................. 548/486
[58] Field of Search ......................................... 548/486

[56] References Cited

U.S. PATENT DOCUMENTS

| | | | |
|---|---|---|---|
| 2,933,503 | 4/1960 | Clark et al. | 548/486 |
| 4,269,989 | 5/1981 | Heise et al. | 548/486 |
| 4,288,442 | 9/1981 | Friebe et al. | 548/486 |
| 4,374,250 | 2/1983 | Hirashima et al. | 548/486 |

FOREIGN PATENT DOCUMENTS

| | | | |
|---|---|---|---|
| 0013859 | 8/1980 | European Pat. Off. | 548/486 |
| 2905876 | 8/1980 | Fed. Rep. of Germany | 548/486 |
| 3124618 | 3/1982 | Fed. Rep. of Germany | 548/486 |
| 57-134470 | 8/1982 | Japan | 548/486 |

OTHER PUBLICATIONS

Gadekar, S. M., *J. Org. Chem.*, 27:1383–1386, (1962).
Schnabel, W. J. et al., *J. Org. Chem.*, 34:1162–1165, (1969).

*Primary Examiner*—Mary C. Lee
*Assistant Examiner*—Robert C. Whittenbaugh

[57] ABSTRACT

Process for the preparation of benzimidazolones of the formula (1)

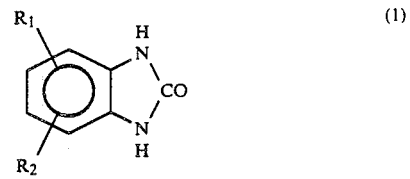

in which $R_1$ and $R_2$ are identical or different and denote hydrogen or halogen atoms, or alkyl($C_1$–$C_4$), alkoxy($C_1$–$C_4$), trifluoromethyl, phenyl, phenoxy or nitro groups, by reacting o-phenylenediamines of the formula (2)

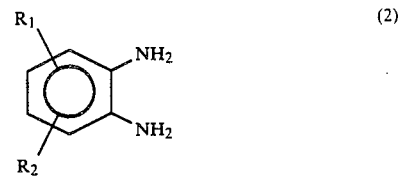

in which $R_1$ and $R_2$ have the meaning given, with phosgene in water in the presence of an alkali metal base or alkaline earth metal base or a salt of an alkali metal hydroxide or alkaline earth metal hydroxide and a weakly inorganic or organic acid or a mixture of such salts or a suitable buffer system, at a pH of about 6 to about 12, and at a temperature of about 20° to 100° C.

9 Claims, No Drawings

PROCESS FOR THE PREPARATION OF BENZIMIDAZOLONES

The invention relates benzimidazolones by reaction of optionally substituted o-phenylenediamines with phosgene in water by carrying out the reaction at a pH of about 6 to about 12.

It is known that benzimidazolone can be prepared in good yields from o-phenylenediamine with urea (European Patent No. 13,859). One disadvantage of this process is the large amount of ammonia automatically formed.

German Patent No. 3,124,618 describes a process in which substituted o-nitroanilines give the corresponding benzimidazolones in a yield of about 90% using carbon monoxide under pressure and with the addition of selenium and a base. Considerable ecological problems also develop in this process because of the selenium used and the use of solvents and organic bases. The reaction of o-phenylenediamine with carbon monoxide using sulfur, triethylamine and tetrahydrofuran is to be viewed in the same light (Japanese Patent No. 57/134,470). Another disadvantage of the abovementioned carbon monoxide processes are the reaction pressures, which means a high expenditure on apparatus becomes necessary. The reaction of o-phenylenediamine with diethyl carbonate leads to benzimidazolone in a conversion of only 15% and is therefore unsuitable for industrial use (German Patent No. 2,528,368, Example 5).

The reaction of substituted o-phenylenediamine with phosgene in water likewise leads to the corresponding benzimidazolones in yields of only 18–62% (German Patent No. 2,905,876, Example 1; European Patent No. 784, Example 1).

The reaction of o-phenylenediamines with phosgene in aqueous hydrochloric acid also leads to a yield of only 60% of the pure benzimidazolones (U.S. Pat. No. 2,933,503, German Patent No. 2,705,892). In this procedure, P. Bouchet et al. (J. Heterocycl. Chem. 15, 625 (1978)) obtained a maximum yield of 80%. If the substituted o-phenylenediamine is reacted with phosgene in sodium hydroxide solution (about 7-fold excess), the corresponding benzimidazolone is obtained in an 80% yield. In addition, with the constantly high pH considerable hydrolysis of phosgene occurs, and salt is therefore additionally obtained (S. M. Gadekar, J. C. Frederik, J. Org. Chem. 27, 1383, (1962)). In organic solvents (see, for example, L. C. March et al., J. Heterocycl. Chem. 7, 39 (1970), W. J. Schnabel et al., J. Org. Chem. 34, 1162 (1969)), the yields are likewise poor, at 60% at the most.

Summarizing, it can be said that in the known phosgene processes for the preparation of benzimidazolones, the yields are generally low. In addition, a significant excess of phosgene is usually necessary.

In contrast, it has now been found that benzimidazolones of the general formula (1)

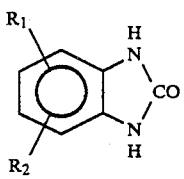

in which $R_1$ and $R_2$ are identical or different and denote hydrogen or halogen atoms, such as, for example, fluorine, chlorine or bromine atoms, or alkyl($C_1$–$C_4$), alkoxy($C_1$–$C_4$), trifluoromethyl, phenyl, phenoxy or nitro groups, can be prepared in good yields and high purities by carrying out the reaction of o-phenylenediamines of the general formula (2)

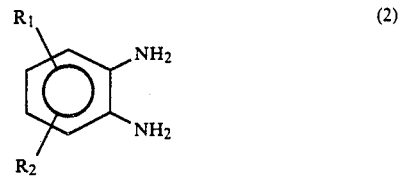

in which $R_1$ and $R_2$ have the abovementioned meanings, with phosgene in water in the presence of an alkali metal base or alkaline earth metal base or a salt of an alkali metal hydroxide or alkaline earth metal hydroxide and a weakly inorganic or organic acid or a mixture of such salts or a suitable buffer system, at a pH of about 6 to about 12, preferably of about 6.5 to about 11 and particularly preferably of about 8 to about 10, and at a temperature of about 20° to 100° C.

At a pH of less than 6.5, evolution of gas and therefore an additional consumption of phosgene occur. In addition, the yield and quality of the benzimidazolones deteriorate at a lower pH. At a pH above 10.5, more than the stoichiometric amounts of alkali metal chloride are formed by the undesirable hydrolysis of phosgene with the aqueous alkali added to keep the pH constant. In addition, at a pH above 10 the benzimidazolones formed remain in the form of their alkali metal salts completely or partly in solution and must be precipitated again by readjusting the pH by means of acid.

An alkali metal base or alkaline earth metal base is used to maintain a constant pH during the reaction of the o-phenylenediamine with phosgene. Aqueous alkali metal hydroxide is preferably employed, and this can be used in the form of a dilute aqueous solution. It is also possible to employ the aqueous solution of an alkali metal salt of a weak mineral acid or organic acid, such as, for example, an alkali metal carbonate, alkali metal bicarbonate or alkali metal acetate. In principle, it is also possible for the desired pH to be established with suitable buffer solutions, for example with a phosphate or acetate buffer solution. However, aqueous sodium hydroxide solution is preferably employed, the concentration being between about 1% and about 50%, in particular between about 20% and about 50%. This solution is metered into the reaction mixture during the reaction of the o-phenylenediamine employed with phosgene at a rate such that the desired pH remains constant during the reaction.

It is surprising in the process according to the invention that virtually no phosgene is decomposed by the water or base present, which is why only stoichiometric amounts of phosgene and alkali are consumed, in accordance with the general equation

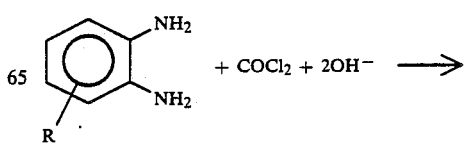

-continued

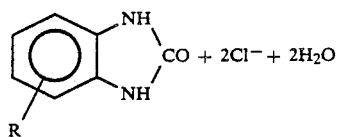

The benzimidazolones, which are completely precipitated in the process according to the invention, can be isolated directly by filtration and washed salt-free with water.

The process according to the invention is described in more detail below.

o-Phenylenediamine or substituted o-phenylenediamines are dissolved in water at a temperature between about 20° and 100° C., preferably between about 70° and 100° C. The concentration of the o-phenylenediamine solution here depends on the solubility of the particular diamine at the chosen temperature. The concentration of the solutions is in general in the range between 5 and 30 per cent by weight. Higher concentrations and therefore suspensions of the optionally substituted o-phenylenediamines can on principle also be used, but under certain circumstances this can lead to a phosgene consumption beyond the stoichiometric amount. However, the yields and purity of the products remain equally good. It is on principle likewise possible to use lower concentrations, but this is inappropriate for economic reasons. As already mentioned, however, the pH during the reaction of the optionally substituted o-phenylenediamines is of decisive importance for the process according to the invention.

The molar ratio of o-phenylenediamine to phosgene varies between 1:1 and not more than 1:1.5, preferably between 1:1 and 1:1.2.

The molar ratio of o-phenylenediamine to alkali metal base or alkaline earth metal base is 1:1 to not more than 1:3, preferably 1:2 to 1:2.4.

The process according to the invention can be carried out either under normal pressure or under increased pressure.

The process according to the invention represents a considerable improvement over the processes which belong to the prior art, which applies both to the yields (>90%) and purity (high purity) of the resulting benzimidazolones and to the ecological aspect, since with the process according to the invention it is possible to keep the phosgene consumption approximately stoichiometric by the controlled pH procedure and therefore to limit the amount of alkali metal chloride automatically obtained to a minimum.

The following examples serve to illustrate the invention without limiting it to these.

EXAMPLE 1 (Benzimidazol-2-one)

100 g (1.01 mol) of phosgene are passed into 108 g (1 mol) of o-phenylenediamine in 450 ml of water at 80° C. over a period of 4 hours, and the pH is kept constant at 10 by simultaneous metering in of 407 g (2.04 mol) of 20% strength aqueous sodium hydroxide solution. The end point of the reaction is determined by sampling for diazotizable amine. After cooling, the product which has precipitated is filtered off with suction, washed with water and dried. 131 g of benzimidazolone of melting point 308° C., which corresponds to a yield of 98% of theory, are obtained in this manner.

EXAMPLE 2 (Benzimidazol-2-one)

100 g (1.01 mol) of phosgene are passed into 108 g (1 mol) of o-phenylenediamine in 800 ml of water at 80° C. over a period of 4 hours and the pH is kept constant at 6.5 by simultaneous metering in of 231 g (1.9 mol) of 50% strength aqueous sodium hydroxide solution. After filtration with suction and washing with water, 126 g of benzimidazol-2-one are obtained, which corresponds to a yield of 94% of theory.

EXAMPLE 3 (5-Methyl-benzimidazol-2-one)

53 g (0.54 mol) of phosgene are passed into 61 g (0.5 mol) of 4-methyl-1,2-diaminobenzene in 450 ml of water and the pH is simultaneously kept constant at 7.2 with 86 g (1.08 mol) of 50% strength aqueous sodium hydroxide solution. After cooling, 72 g of precipitated 5-methyl-benzimidazol-2-one of melting point 290° C. are obtained, which corresponds to a yield of 97% of theory.

EXAMPLE 4 (5-Chlorobenzimidazol-2-one)

115 g (1.16 mol) of phosgene and 459.2 g (2.3 mol) of 20% strength aqueous sodium hydroxide solution are passed and metered at a pH of 8.0 into a solution of 142 g (1 mol) of 4-chloro-1,2-diaminobenzene in 1 l of water at 80° C. as described in Example 1. 161.5 g of 5-chlorobenzimidazol-2-one of melting point 320° C., which corresponds to a yield of 96% of theory, are isolated.

EXAMPLES 5-10

As described in Example 1, phosgene and sodium hydroxide solution were simultaneously passed and metered into 1 mol of substituted o-phenylenediamine in 1 l of water and the pH was kept constant at 7.5. The results are summarized in the following table.

| Substituted o-phenylenediamine | Yield of substituted benzimidazolone | Melting point |
| --- | --- | --- |
| ![F-C6H3(NH2)2] | 98.6% | 300° C. |
| ![O2N-C6H3(NH2)2] | 95.7% | 298° C. |
| ![CH3O-C6H3(NH2)2] | 98.5% | 256° C. |
| ![CH3-C6H3(NH2)2] | 96.9% | 300° C. |
| ![Cl,Cl-C6H2(NH2)2] | 95.3% | >340° C. |

| Substituted o-phenylenediamine | Yield of substituted benzimidazolone | Melting point |
|---|---|---|
| 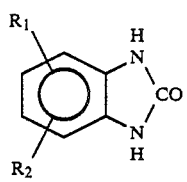 | 97.3% | >340° C. |

We claim:

1. A process for the preparation of a benzimidazolone of the formula (1)

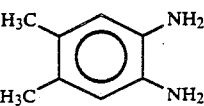

in which $R_1$ and $R_2$ are identical or different and denote hydrogen or halogen atoms, or alkyl($C_1$–$C_4$), alkoxy($C_1$–$C_4$), trifluoromethyl, phenyl, phenoxy or nitro groups, which comprises reacting an o-phenylenediamine of the formula (2)

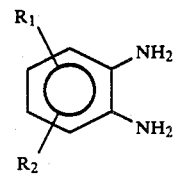

in which $R_1$ and $R_2$ have the abovementioned meanings, with phosgene in water in the presence of an alkali metal base or alkaline earth metal base or a salt of an alkali metal hydroxide or alkaline earth metal hydroxide and a weakly inorganic or organic acid or a mixture of such salts or a suitable buffer system, at a pH of about 6 to about 12, and at a temperature of about 20° to 100° C.

2. The process as claimed in claim 1, wherein the reaction is carried out at a pH of about 6.5 to about 11.

3. The process as claimed in claim 1, wherein the reaction is carried out at a pH of about 8 to about 10.

4. The process as claimed in claim 1, wherein the reaction is carried out in the presence of an aqueous sodium hydroxide solution.

5. The process as claimed in claim 1, wherein the reaction is carried out at a temperature of about 70° to 100° C.

6. The process as claimed in claim 1, wherein said o-phenylenediamine and phosgene are present in a molar ratio ranging from 1:1 to 1:1.5.

7. The process as claimed in claim 1, wherein said o-phenylenediamine and phosgene are present in a molar ratio ranging from 1:1 to 1:1.2.

8. The process as claimed in claim 1, wherein said o-phenylenediamine and alkali metal base or alkaline earth metal base is present in a molar ratio ranging from 1:1 to 1:3.

9. The process as claimed in claim 1, wherein said o-phenylenediamine to alkali metal base or alkaline earth metal base is present in a molar ratio ranging from 1:2 to 1:2.4.

* * * * *